United States Patent [19]
Scheller et al.

[11] Patent Number: 5,807,242
[45] Date of Patent: Sep. 15, 1998

[54] MICROSURGICAL LASER PROBE WITH HOMOGENEOUS LASER LIGHT FIELD

[75] Inventors: Gregg D. Scheller; Michael D. Auld, both of Chesterfield, Mo.

[73] Assignee: Synergetics, Inc., Chesterfield, Mo.

[21] Appl. No.: 823,371

[22] Filed: Mar. 24, 1997

[51] Int. Cl.⁶ .................................................. A61B 17/36
[52] U.S. Cl. ........................... 600/182; 600/180; 385/32; 385/28; 385/117
[58] Field of Search ..................................... 600/130, 132, 600/160, 161, 178, 180, 182; 385/28, 32, 115, 117, 84; 362/32; 606/4, 15

[56] References Cited

U.S. PATENT DOCUMENTS

| | | |
|---|---|---|
| 4,537,193 | 8/1985 | Tanner . |
| 4,813,400 | 3/1989 | Washizuka et al. ..................... 600/182 |
| 5,323,766 | 6/1994 | Uram . |
| 5,356,407 | 10/1994 | Easley et al. . |
| 5,394,499 | 2/1995 | Ono et al. ................................ 385/115 |
| 5,408,551 | 4/1995 | Van Woesik .............................. 385/28 |
| 5,553,177 | 9/1996 | Hering et al. ............................. 385/32 |
| 5,594,825 | 1/1997 | Kawasaki et al. ........................ 385/28 |
| 5,602,948 | 2/1997 | Currie .................................... 385/115 |

*Primary Examiner*—Gene Mancene
*Assistant Examiner*—Ira Hatton
*Attorney, Agent, or Firm*—Howell & Haferkamp, L.C.

[57] ABSTRACT

A microsurgical laser probe used primarily in endoscopic surgery in which the pattern of laser light projected by the probe is improved from a pattern having areas of varying light intensity to a pattern of more uniform light intensity.

21 Claims, 3 Drawing Sheets

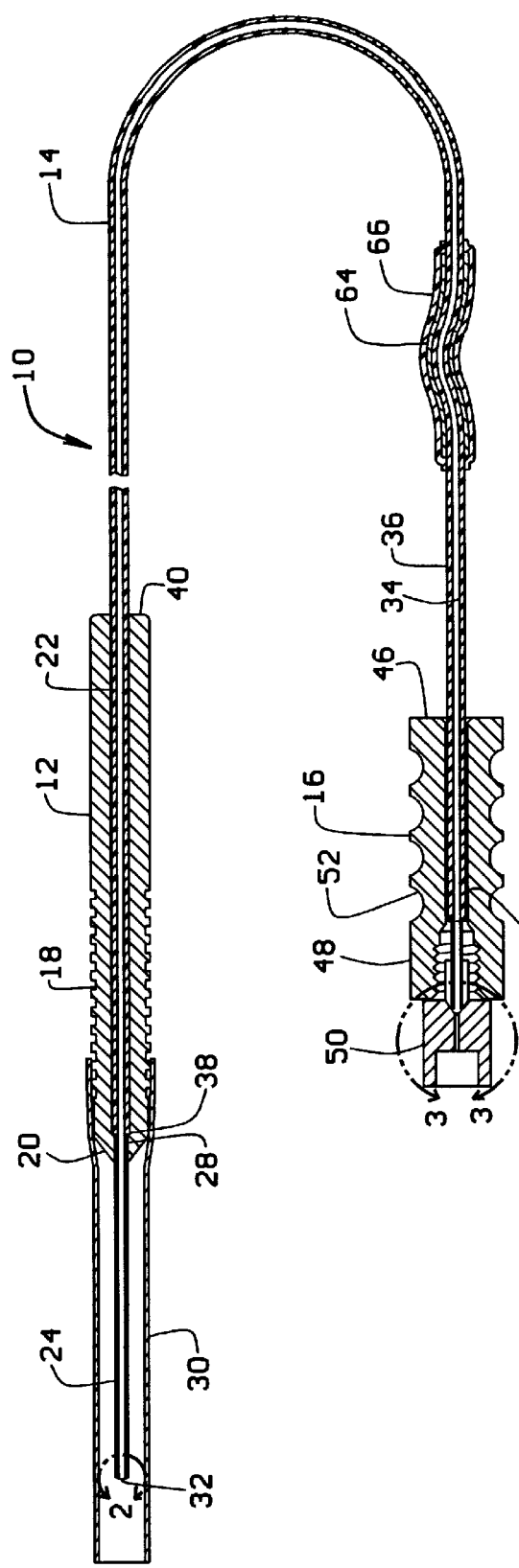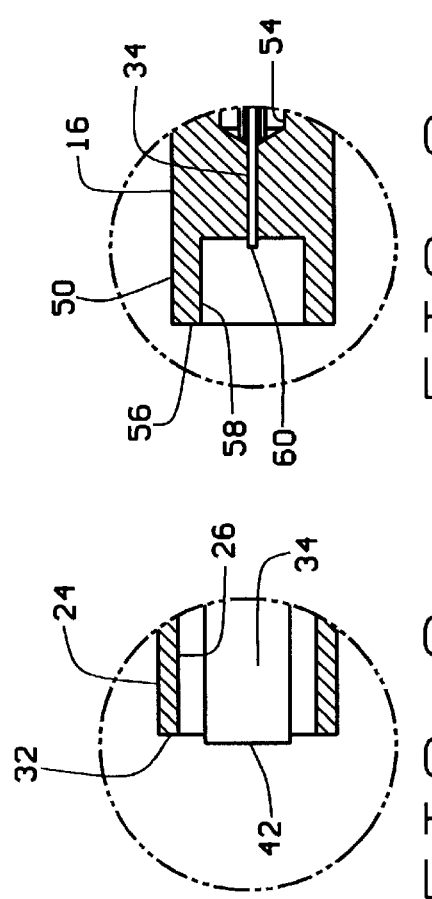

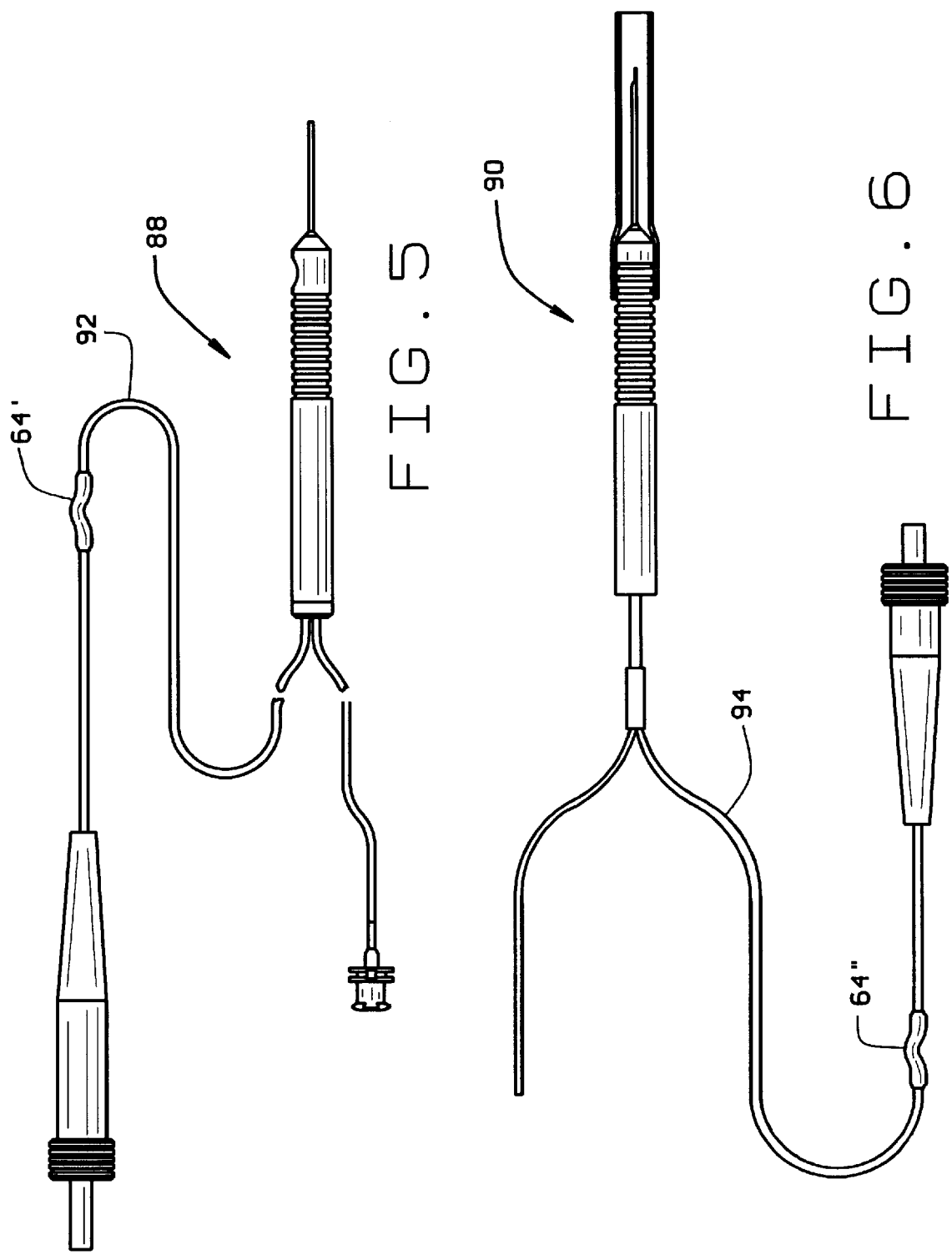

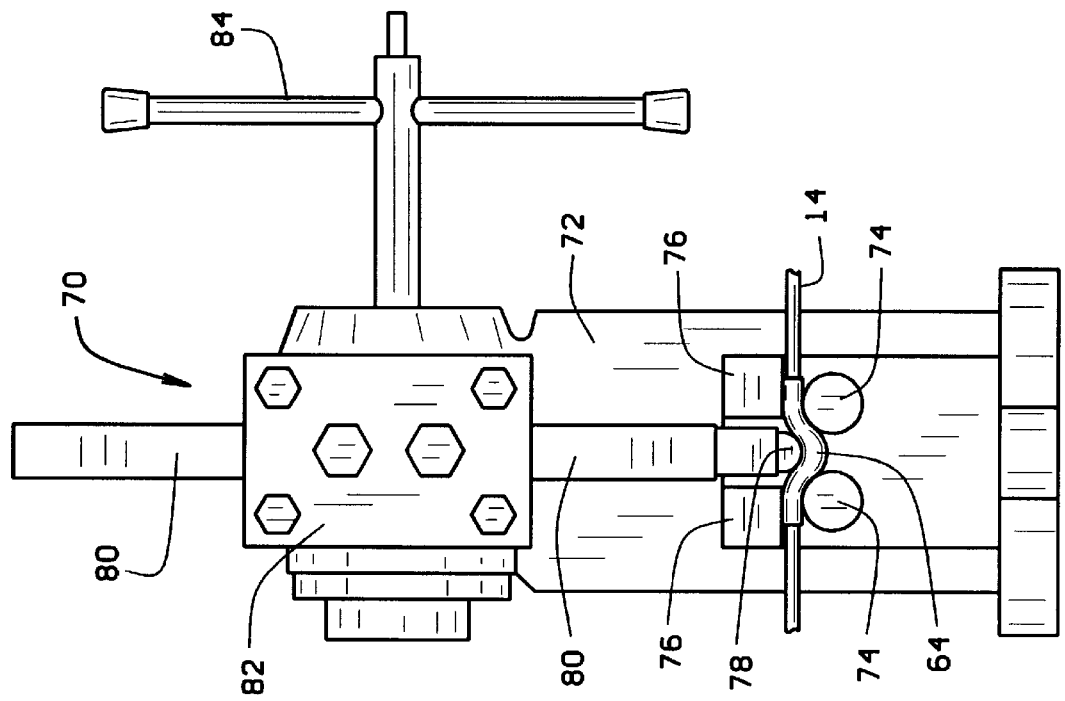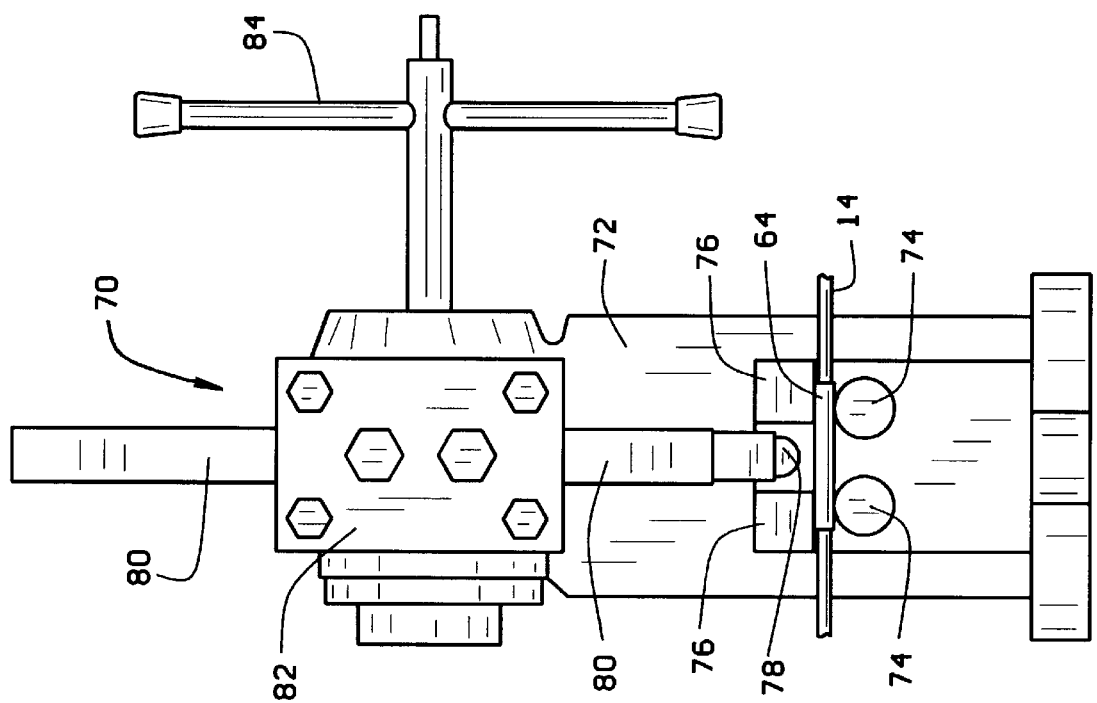

5,807,242

MICROSURGICAL LASER PROBE WITH HOMOGENEOUS LASER LIGHT FIELD

BACKGROUND OF THE INVENTION (1) Field of the Invention

The present invention pertains to a microsurgical laser probe used primarily in endoscopic surgery in which the pattern of laser light projected by the probe is improved from a pattern having areas of varying light intensity to a pattern of more uniform light intensity.

(2) Description of the Prior Art

In endoscopic surgery various different types of instruments are available for use by the surgeon to transmit laser energy to a surgical site in the interior of an organ or body tissue. Many instruments of this type are communicated with a laser source by one or more optic fiber members. Examples of these are disclosed in the U.S. patents of Tanner No. 4,537,193; Uram No. 5,323,766; and Easley et al. No. 5,356,407.

Each of these various different types of endoscopic laser probes employs one or more optic fiber members. Each optic fiber member communicates with a source of laser light at its proximal end and extends into a surgical instrument at its distal end. The optic fiber members convey the laser light from the laser light source to the instrument. The conveyed laser light is projected from the distal end of the optic fiber members to the surgical site in a body organ or tissue.

It has been observed in laser probes of this type that the pattern of laser light projected from the optic fiber distal end is not consistent among laser probes of the same type. Generally, the pattern of laser light projected from the distal ends of the optic fibers is circular. It is desirable that the projected pattern of light have the same intensity of illumination in all areas of the circle. However, not all optic fibers convey laser light to the same extent and at times the pattern of light emitted from an optic fiber will not be uniform. For example, the periphery of the circular pattern of laser light projected from an optic fiber may be more intensely illuminated than the center area of the light pattern. In the manufacture of optic fiber laser probes, the probes with non-uniform laser light patterns are usually detected by the manufacturer's quality control procedures and discarded, resulting in a loss to the manufacturer. This loss could be eliminated if a microsurgical laser probe having a non-uniform laser light pattern could be improved by changing the laser light pattern to a more uniform pattern.

SUMMARY OF THE INVENTION

The present invention provides a method and apparatus for improving the pattern of projected laser light from an optic fiber laser probe having a non-uniform laser light pattern by changing the laser light pattern to a more uniform, homogeneous pattern. The method and apparatus may be practiced with a variety of different types of endoscopic laser probes that rely on one or more optic fibers to convey laser light from a laser light source to a surgical instrument from which the illumination pattern is projected. Although the described embodiment of the invention is practiced with laser probes, it is also applicable to microsurgical illuminators that convey light by optic fibers and the references to laser probes herein should also be interpreted to include other types of optic fiber illuminators.

The apparatus of the invention is a brace that is attached according to the method of the invention to a portion of the optic fiber member or members conveying laser light from the light source to the instrument. The brace holds a bend formed in the portion of the optic fiber member or members and maintains that bend. The inventors have discovered that by bending a portion of the optic fiber or fibers in this manner, and maintaining the bend in the optic fiber or fibers with the brace, the laser light pattern projected from the instrument is improved from the non-uniform pattern that was more intensely illuminated around its periphery to a more uniform pattern having a substantially homogeneous distribution of light intensity within the periphery of the pattern.

BRIEF DESCRIPTION OF THE DRAWINGS

Further objects and features of the present invention are revealed in the following detailed description of the preferred embodiment of the invention and in the drawing figures wherein:

FIG. 1 shows a laser probe to which the apparatus has been assembled according to the method of the invention to improve the laser light projection pattern of the probe;

FIG. 2 shows the detail of the tip of the laser probe;

FIG. 3 shows the detail of the proximal end of the laser probe;

FIG. 4 is a partial sectioned view of the apparatus of the invention shown in FIG. 1;

FIG. 5 shows a further embodiment of a laser probe employing the apparatus of the invention assembled to the probe according to the method of the invention;

FIG. 6 shows a further embodiment of a laser probe having the apparatus of the invention assembled to the probe according to the method of the invention;

FIG. 7 shows a tool employed in practicing the method of the invention; and

FIG. 8 shows the tool of FIG. 7 in a second position of the tool.

DESCRIPTION OF THE PREFERRED EMBODIMENT

FIG. 1 shows an ophthalmic surgery laser probe having the apparatus of the invention assembled thereto according to the method of the invention. Although the apparatus and method of the invention are described with reference to a laser light probe, it should be understood that the apparatus and method of the invention are equally well suited for other types of instruments which employ an optic fiber member to transmit light from a source of illumination to the instrument and references to the laser probes herein should also be interpreted to include other types of optic fiber instruments. The laser probe 10 is generally comprised of a hand piece 12, an optic fiber member 14, and a light source connector 16. The optic fiber member extends into the hand piece at its distal end and into the light source connector at its proximal end.

The hand piece 12 is preferably constructed of plastic to reduce its costs and has the general dimensions of a pencil which gives it a familiar feel to the surgeon's hand that is more easily and comfortably manipulated. Circular serrations 18 extend around the hand piece toward its distal end 20 providing a gripping surface. A hollow internal bore 22 extends axially through the center of the hand piece.

An elongated tubular probe tip 24 extends from the hand piece distal end 20. The interior bore 26 of the probe tip is coaxial with and communicates with the internal bore 22 of the hand piece. Preferably, the probe tip is constructed of stainless steel. A proximal end 28 of the tip extends into the hand piece distal end 20 and is secured thereto.

A flexible plastic sheath 30 is secured over the distal end of the hand piece 20 and extends from the hand piece beyond the distal end 32 of the probe tip. The sheath 30 is stretch fit over the hand piece distal end 20 and is employed in protecting the probe tip. When the laser probe is in use, the sheath 30 is removed and discarded.

The optic fiber member 14 is commercially available and is preferably constructed of a single optic fiber 34 of silica glass at its inner core. A silicon covering or sheath surrounds the optic fiber 34 and this covering in turn is surrounded by a layer of Tefzel®. This optic fiber construction is in turn covered by a polyvinylchloride tubing or cladding 36. At the distal end 38 of the optic fiber member 14, the optic fiber inner core 34 surrounded by the cladding 36 enters the hand piece interior bore 22 at the hand piece proximal end 40. The cladding 36 extends through the hand piece interior bore up to the proximal end 28 of the probe tip where the cladding ends. The optic fiber inner core 34 continues through the internal bore 26 of the probe tip and projects a slight distance beyond the probe tip distal end 32 as shown in FIG. 2. The surface 42 at the distal end of the optic fiber 34 is polished to improve its ability to project laser light.

The proximal end 44 of the optic fiber member 14 enters the distal end 46 of the light source connector 16. The light source connector 16 is preferably constructed of metal and has a hand grip portion 48 and a male plug portion 50. The hand piece portion 48 is provided with circular grooves 52 providing a grip for inserting the plug portion 50 into the laser light source (not shown). An internal bore 54 extends through the connector from its distal end 46 to its proximal end 56. The proximal end 44 of the optic fiber member extends into the connector bore 54 at the connector distal end. At an intermediate portion of the connector inner bore, the cladding 56 ends and the optic fiber inner core 34 extends through the remainder of the connector bore 54 and emerges in a cavity 58 of the connector plug portion 50. The connector plug portion 50 and cavity 58 properly position the proximal end 60 of the optic fiber relative to the laser light source (not shown) to align the laser beam of the laser light source with the optic fiber proximal end.

The above described construction of the laser probe is for the most part conventional. As explained earlier, from time to time in the manufacture of laser probes of this type, a laser probe will be encountered which does not project a uniform pattern of laser light from the optic fiber core at the probe tip. The ideal pattern of laser light projection is a circle having a uniform intensity of light in all areas of the circle. The imperfect pattern of laser light illumination has a greater light intensity around the periphery of the circular projection. With the light intensity being greater at the periphery of the laser projection, it can be appreciated that the heat energy produced by the laser light projected from an imperfect probe will not be consistent in all areas of the laser light projected.

The apparatus of the invention improves the laser light projection pattern of imperfect laser probes so that the non-uniform laser light intensity initially projected by the probe is made more uniform and thereby the heat energy produced by the projected laser light is made more uniform across the pattern of projected laser light. The apparatus 64 is basically a brace that is attached to the exterior of the optic fiber member 14 and is bent to hold the portion of the optic fiber member on which the brace is attached in a bent configuration. The brace 64 is shown in FIGS. 1 and 4 and in its preferred form is a tubular sleeve of annealed stainless steel. However, it should be appreciated that the brace can be given different configurations which would also function to be bent and thereby form a bend in the portion of optic fiber member 14 and maintain the bend formed in the optic fiber 34. In the preferred embodiment of the invention constructed according to the method of the invention, the tubular brace or sleeve 64 is slipped over the exterior cladding or tubing 36 of the optic fiber member 14. The brace is positioned on the optic fiber member before the member is assembled to the hand piece 12 and light source connector 16. A polyolefin sheath or sleeve 66 is also assembled over the optic fiber member 14 before the member's opposite ends are assembled to the hand piece 12 and the light source connector 16. The sheath 66 is then shrink-fit over the brace. The brace 64 is then gradually bent while the light source connector 16 is connected to a laser light source and the laser light projected from the probe tip distal end 32 is observed on a projection surface. It has been observed by the inventors that while the brace is gradually bent, the pattern of laser light projected from the imperfect laser probe will gradually diffuse and change from the initial pattern of projected light having a greater intensity around its periphery than at its center, to a more uniform pattern of projected light having substantially the same light intensity throughout the circular projected pattern. In this manner, an imperfect laser probe that in the past would likely be discarded by the manufacturer can be corrected by improving its pattern of projected laser light.

FIGS. 7 and 8 show a simple tool construction that can be employed in practicing the method of the invention. The tool 70 functions in substantially the same manner as a drill press and will only be generally described. Basically, the tool comprises a base 72 that supports a pair of cylindrical anvils 74 that project forwardly from the base and a pair of rectangular arms 76 that also project forwardly from the base. The arms 76 are spaced above the anvils 74 a sufficient distance to enable insertion of the portion of the fiber optic member 14 having the brace 64 and sheath 66 secured thereto into the spacing between the anvil and arms. A press 78 having a rounded bottom surface is connected to the bottom end of a rack 80 that extends through a gear box 82 of the tool. A hand wheel 84 extends into the gear box 82 and is operatively connected by a transmission (not shown) within the gear box to control upward and downward movement of the toothed rack 80 in response to rotation of the hand wheel in opposite directions of rotation. By turning the hand wheel 84 in one direction, the rack 80 is lowered between the arms 76, and by rotating the hand wheel in the opposite direction the rack 80 is raised above the arms 76.

In use of the tool, the portion of the optic fiber member 14 having the brace 64 and sheath 66 secured thereto is positioned between the arms and anvils as shown in FIG. 7. The light source connector 16 is then subjected to a source of laser light (not shown) and the pattern of light projected from the tip distal end 32 is observed. The hand wheel 84 of the tool is then turned to cause the rack 80 to gradually lower and thereby gradually cause the press 78 to come into engagement with the brace 64 wrapped by the sheath 66 on the optic fiber member 14. The press 78 is continued to be lowered while the laser light projection pattern is observed, gradually causing the brace 64 to bend and thereby bend the portion of the optic fiber member 14 on which the brace is attached. The bending process continues while observing the pattern of laser light illumination until the pattern changes from its original non-uniform pattern to a more uniform pattern of laser light intensity. When the more uniform pattern of light is achieved, the hand wheel is then turned in the opposite direction raising the toothed rack 80 and the press 78. The portion of the optic fiber member 14 of the now improved laser probe is then removed from the tool, thus completing the process.

FIGS. 5 and 6 show additional types of laser probes on which the apparatus and the method of the invention may be employed to improve the laser light projection pattern if needed. In FIG. 5 an aspiring laser probe 88 is shown and in FIG. 6 an illuminated laser probe 90 is shown. In both of these further embodiments, the brace 64' is shown attached to the optic fiber member 92 of the aspirating laser probe in the same manner as described above, and the brace 64' is applied to the optic fiber member 94 of the illuminated laser probe in substantially the same manner as described above. These additional embodiments of laser probes are shown to emphasize that the apparatus and method of the invention may be employed on any endoscopic surgical instrument employed optic fiber members to convey laser light or other types of light, where it is desirable to improve the projected pattern of laser light or other light from a pattern having a non-uniform pattern of intensity to a more uniform pattern of intensity.

While the present invention has been described by reference to a specific embodiment, it should be understood that modifications and variations of the invention may be constructed without departing from the scope of the invention defined in the following claims.

What is claimed is:

1. An illuminator comprising:

an instrument handle;

an optic fiber having opposite proximal and distal ends, the distal end extending into the instrument handle;

a brace on a portion of the optic fiber between its proximal and distal ends, the brace maintaining a bend formed in the portion of the optic fiber and except for the portion of the optic fiber the brace is on, the optic fiber between the instrument handle and the optic fiber proximal end is flexible.

2. The illuminator of claim 1, wherein:

the brace is formable and has been bent to form the bend in the portion of the optic fiber.

3. The illuminator of claim 1, wherein:

the brace is a rigid sleeve that extends around the portion of the optic fiber, a bend is formed in the sleeve and the sleeve bend maintains the bend formed in the portion of the optic fiber.

4. The illuminator of claim 1, wherein:

the illuminator is a laser probe.

5. The illuminator of claim 1, wherein:

a tubular probe projects from the instrument handle and the distal end of the optic fiber extends through the handle and into the tubular probe.

6. The illuminator of claim 5, wherein:

a connector for attaching the optic fiber proximal end to a source of illumination is on the optic fiber proximal end, and the portion of the optic fiber the brace is on is between the instrument handle and the connector.

7. The illuminator of claim 1, wherein:

a cladding surrounds the optic fiber and the brace is on the cladding.

8. The illuminator of claim 7, wherein:

the optic fiber is the only optic fiber surrounded by the cladding.

9. The illuminator of claim 7, wherein:

the brace is a rigid tube mounted on the cladding of the portion of the optic fiber and the rigid tube has a bend that maintains the bend formed in the portion of the optic fiber.

10. The illuminator of claim 9, wherein:

the rigid tube is a metal tube.

11. A microsurgical illuminator comprising:

an instrument handle having opposite proximal and distal ends;

a tubular probe projecting from the instrument handle distal end to a distal end of the probe;

at least one flexible, optic fiber having opposite proximal and distal ends, the distal end of the optic fiber enters the instrument handle at the instrument handle proximal end and extends through the instrument handle and into the probe;

a connector on the optic fiber proximal end for attaching the optic fiber proximal end to an illumination source; and, a brace on a portion of the optic fiber between the instrument handle and the connector, the brace maintaining a bend formed in the portion of the optic fiber.

12. The microsurgical illuminator of claim 11, wherein:

a protective cladding surrounds the optic fiber between its proximal and distal ends, and the optic fiber is the only optic fiber surrounded by the protective cladding.

13. The microsurgical illuminator of claim 12, wherein:

the brace is attached onto the protective cladding of the portion of the optic fiber.

14. The microsurgical illuminator of claim 11, wherein:

the brace is formable and has been bent to form the bend in the portion of the optic fiber.

15. The microsurgical illuminator of claim 11, wherein:

the brace is a rigid sleeve that extends around the portion of the optic fiber, a bend is formed in the sleeve and the bend in the sleeve maintains the bend formed in the portion of the optic fiber.

16. The microsurgical illuminator of claim 14, wherein:

the rigid sleeve extends completely around the portion of the optic fiber.

17. The microsurgical illuminator of claim 11, wherein:

the brace is a rigid tube that extends around the cladding of the portion of the optic fiber, a bend is formed in the tube and the bend in the tube maintains the bend formed in the portion of the optic fiber.

18. The microsurgical illuminator of claim 11, wherein:

the illuminator is a laser probe.

19. A method of making more uniform a pattern of illumination projected from a distal end of an optic fiber having opposite proximal and distal ends, the method comprising the steps of:

providing a brace on a portion of the optic fiber between its proximal and distal ends;

subjecting the proximal end of the optic fiber to a source of illumination causing the optic fiber to convey the illumination through the optic fiber from its proximal end to its distal end;

projecting the illumination from the optic fiber distal end as an initial pattern of illumination on a surface;

gradually bending the portion of the optic fiber by bending the brace while observing the initial pattern of illumination projected on the surface until the initial pattern of illumination projected on the surface changes to a more uniform pattern of illumination than the initial pattern of illumination.

20. The method of claim 19, further comprising:

projecting the illumination from the optic fiber distal end as an initial pattern of illumination on the surface where the initial pattern of illumination has a circular configuration that is more intensely illuminated at its periphery than at its center.

21. The method of claim 19, further comprising:

gradually bending the portion of the optic fiber by bending the brace until the initial pattern of illumination changes to a circular pattern having a uniform intensity of illumination.

\* \* \* \* \*